(12) United States Patent
Wallajapet et al.

(10) Patent No.: US 12,207,994 B2
(45) Date of Patent: Jan. 28, 2025

(54) FEMININE HYGIENE ARTICLE WITH IMPROVED LIQUID HANDLING

(71) Applicant: Kimberly-Clark Worldwide, Inc., Neenah, WI (US)

(72) Inventors: Palani Raj R. Wallajapet, Neenah, WI (US); Fehime Vatansever, Neenah, WI (US); Cynthia S. Krueger, Winneconne, WI (US); Richmond R. Cohen, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 997 days.

(21) Appl. No.: 17/056,186

(22) PCT Filed: May 31, 2018

(86) PCT No.: PCT/US2018/035258
§ 371 (c)(1),
(2) Date: Nov. 17, 2020

(87) PCT Pub. No.: WO2019/231444
PCT Pub. Date: Dec. 5, 2019

(65) Prior Publication Data
US 2021/0212865 A1 Jul. 15, 2021

(51) Int. Cl.
*A61F 13/472* (2006.01)
*A61F 13/533* (2006.01)
(Continued)

(52) U.S. Cl.
CPC .......... *A61F 13/472* (2013.01); *A61F 13/533* (2013.01); *A61F 13/535* (2013.01);
(Continued)

(58) Field of Classification Search
CPC .. A61F 13/472; A61F 13/533; A61F 13/5376; A61F 13/538; A61F 2013/4708;
(Continued)

(56) References Cited

U.S. PATENT DOCUMENTS 5,429,630 A * 7/1995 Beal ...................... A61F 13/476
604/389
5,846,230 A 12/1998 Osborn et al.
(Continued)

FOREIGN PATENT DOCUMENTS

CN 1225002 A 8/1999
EP 2810630 B1 2/2018
(Continued)

OTHER PUBLICATIONS

Kuster, J.B., "Diaper core content and performance—A global sampling", Nonwovens World, Feb. 2004, https://www.researchgate.net/publication/293610509_Diaper_core_content_and_performance_-_A_global_sampling.
(Continued)

*Primary Examiner* — Susan S Su
(74) *Attorney, Agent, or Firm* — KIMBERLY-CLARK WORLDWIDE, INC.

(57) ABSTRACT

An absorbent article having a liquid-handling system includes a liquid permeable bodyside liner; a liquid impermeable outer cover; and an absorbent core disposed between the liner and the outer cover, wherein the absorbent core has a longitudinal direction, wherein the absorbent core includes a layer of a three-dimensionally patterned, wetlaid, cellulosic tissue nonwoven material, and wherein the layer includes longitudinal ridges and grooves. The absorbent core can include multiple layers of a three-dimensionally patterned, wetlaid, cellulosic tissue nonwoven material, wherein each layer of the multiple layers includes longitu-
(Continued)

dinal ridges and grooves, and wherein the multiple layers are joined by lines of embossing, such lines of embossing extending in the longitudinal direction. Each layer of the multiple layers can include embossed longitudinal ridges and grooves.

18 Claims, 8 Drawing Sheets

(51) Int. Cl.
  *A61F 13/535* (2006.01)
  *A61F 13/537* (2006.01)
  *A61F 13/538* (2006.01)
  *A61F 13/47* (2006.01)
  *A61F 13/53* (2006.01)
(52) U.S. Cl.
  CPC ........ *A61F 13/5376* (2013.01); *A61F 13/538* (2013.01); *A61F 2013/4708* (2013.01); *A61F 2013/530109* (2013.01); *A61F 2013/53778* (2013.01)
(58) Field of Classification Search
  CPC .......... A61F 2013/530109; A61F 2013/53778; A61F 13/535
  See application file for complete search history.

(56) References Cited

U.S. PATENT DOCUMENTS

| | | | |
|---|---|---|---|
| 5,865,824 A * | 2/1999 | Chen | A61F 13/5323 604/385.12 |
| 6,241,714 B1 * | 6/2001 | Raidel | A61F 13/53717 604/383 |
| 6,486,379 B1 * | 11/2002 | Chen | A61F 13/5323 604/378 |
| 6,503,233 B1 | 1/2003 | Chen et al. | |
| 6,573,424 B1 | 6/2003 | Raidel et al. | |
| 6,617,490 B1 * | 9/2003 | Chen | D04H 1/732 604/385.01 |
| 6,932,798 B2 | 8/2005 | Kudo et al. | |
| 7,132,585 B2 * | 11/2006 | Kudo | A61F 13/53747 604/380 |
| 7,625,363 B2 | 12/2009 | Yoshimasa et al. | |
| 8,575,419 B2 | 11/2013 | Di Virgilio et al. | |
| 8,975,466 B2 | 3/2015 | R. Marcelo et al. | |
| 9,044,356 B2 | 6/2015 | Ng et al. | |
| 9,763,835 B2 | 9/2017 | Becker et al. | |
| 2002/0055726 A1 | 5/2002 | Costa | |
| 2003/0036741 A1 | 2/2003 | Abba et al. | |
| 2003/0096548 A1 | 5/2003 | Groitzsch et al. | |
| 2003/0118780 A1 * | 6/2003 | Adam | D04H 1/732 428/218 |
| 2003/0135181 A1 * | 7/2003 | Chen | A47L 13/20 604/374 |
| 2005/0148970 A1 * | 7/2005 | Kudo | A61F 13/5376 604/378 |
| 2008/0221539 A1 * | 9/2008 | Zhao | A61F 13/535 604/378 |
| 2016/0089281 A1 | 3/2016 | Barbosa et al. | |
| 2019/0374396 A1 * | 12/2019 | Hood | A61F 13/47218 |

FOREIGN PATENT DOCUMENTS

| | | |
|---|---|---|
| JP | 2006271650 A | 10/2006 |
| JP | 2013220286 A | 10/2013 |
| KR | 100458231 B1 | 4/2005 |

OTHER PUBLICATIONS

Medical Textiles, "Chemically cross-linked fluff pulp", May 1999.
Medical Textiles, "Multifunctional absorbent structure for liquid intake, distribution and retention", May 2002.

* cited by examiner

FEMININE HYGIENE ARTICLE WITH IMPROVED LIQUID HANDLING

BACKGROUND

The present disclosure is generally directed to absorbent articles. Absorbent materials (e.g., surge, absorbent core) are indispensable components of absorbent products such as feminine hygiene articles. Absorbent materials are used extensively to complement an absorbent article's gasketing system by serving as reservoirs in a sense to prevent leakage of body fluids from the products. Although the importance of an effective absorbent system is well recognized, improving the construction and structure of an absorbent system is desired.

Current absorbent articles such as feminine hygiene articles are capacity overdesigned to maintain acceptable leakage performance even though only about one-third of the absorbent core is used when the product is discarded after use. The opportunity cost of the underutilized absorbent core is significant. Prior art absorbent articles use a creped tissue material as a wrap sheet or core wrap around the absorbent core. The function of this wrap sheet is to transport superabsorbent material (SAM) and fluff pulp from the absorbent forming to the packaging end of the converting process and to contain SAM in absorbent core. This wrap sheet material provides no liquid management benefit.

SUMMARY

The present disclosure provides a solution for increasing absorbent core utilization efficiency. A solution to this problem is important because reducing and/or eliminating leakage, especially early leakage, is critical to delivering a consistently positive experience to the user. The present disclosure addresses these issues by providing an absorbent core that includes a three-dimensional patterned cellulosic layer.

The present disclosure replaces the absorbent core of a menses-absorbing product with a wet-laid pulp material made using the UCTAD process with a suitable blend of pulp fibers under process conditions that achieve high machine-direction fiber orientation and low density through rush transfer to obtain optimal liquid distribution and retention of menses.

In one aspect, an absorbent article having a liquid-handling system includes a liquid permeable bodyside liner; a liquid impermeable outer cover; and an absorbent core disposed between the liner and the outer cover, wherein the absorbent core has a longitudinal direction, wherein the absorbent core includes a layer of a three-dimensionally patterned, wetlaid, cellulosic tissue nonwoven material, and wherein the layer includes longitudinal ridges and grooves.

In an alternate aspect, an absorbent article having a liquid-handling system includes a liquid permeable bodyside liner; a liquid impermeable outer cover; and an absorbent core disposed between the liner and the outer cover, wherein the absorbent core has a longitudinal direction, wherein the absorbent core includes multiple layers of a three-dimensionally patterned, wetlaid, cellulosic tissue nonwoven material, wherein each layer of the multiple layers includes longitudinal ridges and grooves, and wherein the multiple layers are joined by lines of embossing, such lines of embossing extending in the longitudinal direction.

In another aspect, an absorbent article having a liquid-handling system includes a liquid permeable bodyside liner; a liquid impermeable outer cover; and an absorbent core disposed between the liner and the outer cover, wherein the absorbent core has a longitudinal direction, wherein the absorbent core includes multiple layers of a three-dimensionally patterned, wetlaid, cellulosic tissue nonwoven material, and wherein each layer of the multiple layers includes embossed longitudinal ridges and grooves.

Objects and advantages of the disclosure are set forth below in the following description, or can be learned through practice of the disclosure.

BRIEF DESCRIPTION OF THE DRAWINGS

The present disclosure will be more fully understood, and further features will become apparent, when reference is made to the following detailed description and the accompanying drawings. The drawings are merely representative and are not intended to limit the scope of the claims.

Figure 1:
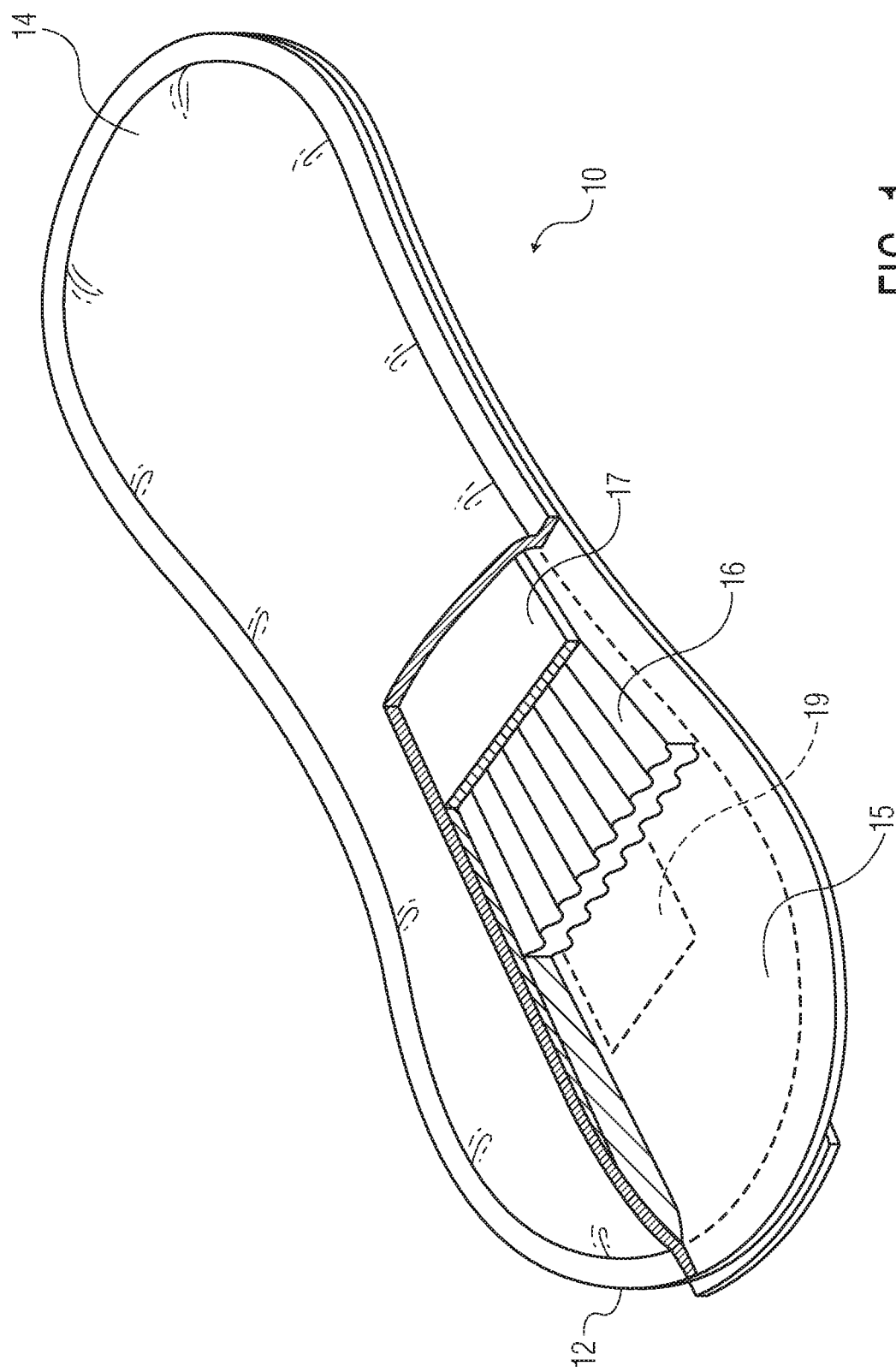
FIG. 1 is perspective, partially-cutaway view of a feminine hygiene product of the present disclosure.

Repeat use of reference characters in the present specification and drawings is intended to represent the same or analogous features or elements of the present disclosure. The drawings are representational and are not necessarily drawn to scale. Certain proportions thereof might be exaggerated, while others might be minimized.

DETAILED DESCRIPTION

As used herein the term "nonwoven fabric or web" refers to a web having a structure of individual polymeric and/or cellulosic fibers or threads that are interlaid, but not in an identifiable manner as in a knitted fabric. Nonwoven fabrics or webs have been formed from many processes such as for example, meltblowing processes, spunbonding processes, bonded carded web processes, those used to make tissue and towels, etc.

As used herein, the term "meltblown web" generally refers to a nonwoven web that is formed by a process in which a molten thermoplastic material is extruded through a plurality of fine, usually circular, die capillaries as molten fibers into converging high velocity gas (e.g. air) streams that attenuate the fibers of molten thermoplastic material to reduce their diameter, which can be to microfiber diameter.

Thereafter, the meltblown fibers are carried by the high velocity gas stream and are deposited on a collecting surface to form a web of randomly dispersed meltblown fibers. Such a process is disclosed, for example, in U.S. Pat. No. 3,849,241 to Butin, et al., which is incorporated herein in its entirety by reference thereto. Generally speaking, meltblown fibers can be microfibers that are substantially continuous or discontinuous, generally smaller than 10 microns in diameter, and generally tacky when deposited onto a collecting surface.

As used herein, the term "spunbond web" generally refers to a web containing small diameter substantially continuous fibers. The fibers are formed by extruding a molten thermoplastic material from a plurality of fine, usually circular, capillaries of a spinnerette with the diameter of the extruded fibers then being rapidly reduced as by, for example, educative drawing and/or other well-known spunbonding mechanisms. The production of spunbond webs is described and illustrated, for example, in U.S. Pat. No. 3,692,618 to Dorschner, et al.; U.S. Pat. No. 3,802,817 to Matsuki, et al.; U.S. Pat. No. 3,338,992 to Kinney; U.S. Pat. No. 3,341,394 to Kinney; U.S. Pat. No. 3,502,763 to Hartman; U.S. Pat. No. 3,502,538 to Levy; U.S. Pat. No. 3,542,615 to Dobo, et al.; U.S. Pat. No. 4,340,563 to Appel, et al.; and U.S. Pat. No. 5,382,400 to Pike, et al.; each of which is incorporated herein by reference to the extent it does not conflict herewith. Spunbond fibers are generally not tacky when they are deposited onto a collecting surface. Spunbond fibers can sometimes have diameters less than about 40 microns, and are often between about 5 to about 20 microns.

As used herein the term "staple fiber" means fibers that have a fiber length generally in the range of about 0.5 to about 150 millimeters. Staple fibers can be cellulosic fibers or non-cellulosic fibers. Some examples of suitable non-cellulosic fibers that can be used include, but are not limited to, hydrophilically-treated polyolefin fibers, polyester fibers, nylon fibers, polyvinyl acetate fibers, and mixtures thereof. Hydrophilic treatments can include durable surface treatments and treatments in polymer resins/blends. Cellulosic staple fibers include for example, pulp, thermomechanical pulp, synthetic cellulosic fibers, modified cellulosic fibers, and the like. Cellulosic fibers can be obtained from secondary or recycled sources. Some examples of suitable cellulosic fiber sources include virgin wood fibers, such as thermomechanical, bleached and unbleached softwood and hardwood pulps. Secondary or recycled cellulosic fibers can be obtained from office waste, newsprint, brown paper stock, and paperboard scrap. Further, vegetable fibers, such as abaca, flax, milkweed, cotton, modified cotton, cotton linters, can also be used as the cellulosic fibers. In addition, synthetic cellulosic fibers such as, for example, rayon, viscose rayon, and lyocell can be used. Modified cellulosic fibers are generally composed of derivatives of cellulose formed by substitution of appropriate radicals (e.g., carboxyl, alkyl, acetate, nitrate, etc.) for hydroxyl groups along the carbon chain. Desirable staple fibers for the purposes of this application are hydrophilic, such as traditional cellulosic fibers (a desirable example of which is pulp fibers, as can be found in rolled tissues and paper-based towels).

As used herein, the term "substantially continuous fibers" is intended to mean fibers that have a length that is greater than the length of staple fibers. The term is intended to include fibers that are continuous, such as spunbond fibers, and fibers that are not continuous, but have a defined length greater than about 150 millimeters.

As used herein "bonded carded webs" or "BCW" refers to nonwoven webs formed by carding processes as are known to those skilled in the art and further described, for example, in U.S. Pat. No. 4,488,928 to Ali Khan et al., which is incorporated herein by reference thereto. Briefly, carding processes involve starting with a blend of, for example, staple fibers with bonding fibers or other bonding components in a bulky ball that is combed or otherwise treated to provide a generally uniform basis weight. This web is heated or otherwise treated to activate the adhesive component resulting in an integrated, usually lofty nonwoven material.

The basis weight of nonwoven webs is usually expressed in ounces of material per square yard (osy) or grams per square meter (gsm) and fiber diameters are usually expressed in microns, or in the case of staple fibers, denier. It is noted that to convert from osy to gsm, multiply osy by 33.91.

As used herein, the terms "machine direction" or "MD" generally refers to the direction in which a material is produced. It is also often the direction of travel of the forming surface onto which fibers are deposited during formation of a non-woven web. The term "cross-machine direction" or "CD" refers to the direction perpendicular to the machine direction. Dimensions measured in the cross-machine direction (CD) are referred to as "width" dimensions, while dimensions measured in the machine direction (MD) are referred to as "length" dimensions. The width and length dimensions of a planar sheet make up the X and Y directions of the sheet. The dimension in the depth direction of a planar sheet is also referred to as the Z-direction.

As used herein, the term "g/cc" generally refers to grams per cubic centimeter as a measure of density and "cc/g" generally refers to cubic centimeters per gram as a measure of Specific Volume, an inverse of density.

As used herein, the term "hydrophilic" generally refers to fibers or films, or the surfaces of fibers or films that are wettable by aqueous liquids in contact with the fibers. The term "hydrophobic" includes those materials that are not hydrophilic as defined. The phrase "naturally hydrophobic" refers to those materials that are hydrophobic in their chemical composition state without additives or treatments affecting the hydrophobicity.

The degree of wetting of the materials can, in turn, be described in terms of the contact angles and the surface tensions of the liquids and materials involved. Equipment and techniques suitable for measuring the wettability of particular fiber materials or blends of fiber materials can be provided by the Cahn SFA-222 Surface Force Analyzer System, or a substantially equivalent system. When measured with this system, fibers having contact angles less than 90 are designated "wettable" or hydrophilic, and fibers having contact angles greater than 90 are designated "nonwettable" or hydrophobic.

The term "composite" as used herein, refers to a film material that has been bonded to or otherwise exists with a nonwoven web including fibers. The film material itself can be mono-layer, multi-component, or multilayer. The composite can be apertured and breathable, or the film material of the composite can be essentially intact.

As used herein, the terms "personal care product" and "absorbent article" refer to any article capable of absorbing liquids. Examples of some absorbent articles include, but are not limited to, personal care absorbent articles such as feminine hygiene products (e.g., sanitary napkins, pad, liners, and the like), and so forth. Materials and processes suitable for forming such absorbent articles are well known to those skilled in the art.

As used herein, the term "rush transfer" refers to transferring a dewatered web from a first transfer fabric to a second transfer fabric travelling at a slower speed than the first transfer fabric (rush transfer) to increase the bulk of the wet web. A speed differential can be provided between fabrics at one or more points of transfer of the wet web. The speed difference between the forming fabric and the transfer fabric can be from about 5 to about 75 percent or greater, preferably from about 10 to about 35 percent, and more preferably from about 15 to about 25 percent, based on the speed of the slower transfer fabric. The optimum speed differential will depend on a variety of factors, including the particular type of product being made. The transfer effects can be imparted to the web using a single differential speed transfer or two or more differential speed transfers of the wet web prior to drying. Hence there can be one or more transfer fabrics. The web is transferred to the last fabric (the throughdrying fabric) for final drying preferably with the assistance of vacuum to ensure macroscopic rearrangement of the web to give the desired bulk and appearance. The step of rush transfer can be performed with many of the methods known in the art, particularly those for example disclosed in U.S. Pat. No. 5,830,321 to Lindsay et al.; U.S. Pat. No. 6,080,691 to Lindsay et al.; U.S. Pat. No. 5,667,636 to S. A. Engel et al.; and U.S. Pat. No. 5,607,551 to T. E. Farrington, Jr. et al.; each of which is incorporated herein by reference to the extent it does not conflict herewith.

As used herein, "UCTAD" and "uncreped, through-air dried" material refers to the material described in U.S. Pat. No. 5,048,589 to Cook et al.; U.S. Pat. No. 5,399,412 to Sudall et al.; U.S. Pat. No. 5,667,636 to Engel et al.; and U.S. Pat. No. 6,808,790 to Chen et al.; each of which is incorporated herein by reference to the extent it does not conflict herewith.

As used here, "menses simulant" refers to the artificial liquid used to simulate human menses in the testing of feminine hygiene products. Examples are described in U.S. Pat. No. 5,883,231 to Achter et al.; U.S. Pat. No. 6,060,636 to Yahiaoui, et al.; and U.S. Pat. No. 6,627,789 to VanDen-Bogart, et al.; each of which is incorporated herein by reference to the extent it does not conflict herewith.

Disposable absorbent products are designed to be removed and discarded after a single use. By single use it is meant that the disposable absorbent product will be disposed of after being used once instead of being laundered or cleaned for reuse, as is typical of regular cloth underwear.

The present disclosure describes personal care products and absorbent products that incorporate an improved liquid handling system. The control of liquid in personal care products is of particular interest to those who use them. The desire to avoid leakage is important to consumers of these products. One aspect of controlling liquid handling addresses the tendency of an absorbent article to become saturated in a target insult area. Increasing the capability of an absorbent article to move liquid away from the target insult area can help to limit saturation and improve the overall liquid-handling performance of the absorbent article. More specifically, an absorbent article capable of moving liquid from the target insult area, thereby reducing saturation in the target insult area, can improve insult intake, particularly in situations where more than one insult is voided such as third insult intake.

The present disclosure improves absorbent core utilization efficiency such that less absorbent material is needed, resulting in cost savings. The liquid transport is enabled by using uncreped through-air dried (UCTAD) nonwoven material as an absorbent core in absorbent articles to distribute liquid from the target insult area. UCTAD is a three-dimensionally patterned, wetlaid, cellulosic tissue nonwoven material. Described herein are ranges of UCTAD properties such as basis weight, textured surface, density, and fiber composition that improve third insult intake time by moving liquid from a target insult area.

In various aspects of the disclosure, an absorbent article can include components such as: a liquid-permeable layer (e.g., bodyside liner, surge layer, etc.), a liquid-impermeable layer that can have moisture vapor permeability or breathability (e.g., outer cover, ventilation layer, baffle, etc.), an absorbent core, and so forth as is well-known to one of skill in the art.

For purposes of illustration only, certain personal care absorbent products are described herein. This should be considered illustrative only as the absorbent core of the present disclosure can be used in all types of personal care absorbent products including, but not limited to, diapers, training pants, incontinence garments, sanitary napkins, bandages, and the like.

Figure 2:
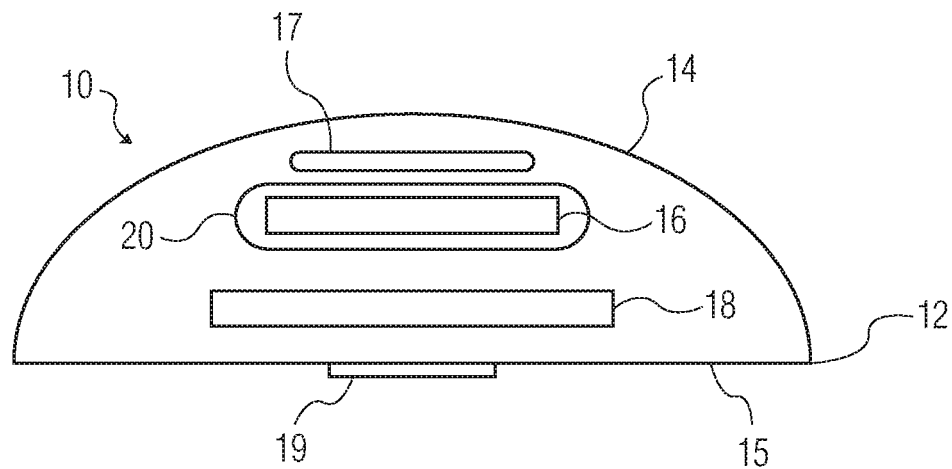
FIG. 2 is an elevation schematic view of a cross-section of the feminine hygiene product of FIG. 1, simplified to illustrate the primary components.

For example, disposable absorbent articles include feminine hygiene pads such as the pad 10 shown in FIGS. 1 and 2. Pad 10 includes a bodyside liner 14 and a baffle or outer cover 15 that extend to a pad perimeter 12. The pad 10 can include an absorbent core 16 and a transfer or surge layer 17 disposed between the bodyside liner 14 and the baffle or outer cover 15. The absorbent core 16 is described in more detail below. Many products also have an adhesive strip 19 to help hold the product in place during use by adhering it to the user's underclothes.

The absorbent core 16 has a body-facing surface adjacent the bodyside liner 14, a garment-facing surface adjacent the outer cover 15, and a pair of longitudinal sides. The bodyside liner 14 is at the top of FIG. 2. The bodyside liner 14 is designed to allow body fluid to quickly pass through and be received by an absorbent core 16. The bodyside liner 14 is placed in contact with the genital area of a human body. An optional surge layer 17 is positioned below the liner 14 and above the absorbent core 16. The surge layer 17 acts as a reservoir to accept large surges of liquid and slowly release them to the subsequent layers. Below the surge layer 17 is the absorbent core 16. Under the absorbent core 16 is a baffle or outer cover 15. Further, in one aspect, there is an optional second absorbent layer, such as the airlaid layer 18 seen in FIG. 2. Airlaid layer 18 can be placed either below the absorbent core 16 as shown, or above the absorbent core 16. Finally, the absorbent article 10 can also include a core wrap 20 surrounding the absorbent core 16 to in part contain the materials of the absorbent core 16.

Pads typically have a thickness of about 2.5 centimeters (cm) or less. Desirably, the thickness of a pad is less than about 1 cm. More desirably, the thickness of a pad is less than about 0.7 cm. A pad can have a length of from between about 15 cm to about 50 cm, and a width of from between about 2 cm to about 15 cm. Pads can have a rectangular, hourglass, or asymmetrical configuration.

A surge layer 17 helps to absorb, decelerate, and diffuse surges or gushes of liquid that might be rapidly introduced into the absorbent article. The surge layer 17 can rapidly accept and temporarily hold the liquid prior to releasing the liquid into, for instance, the absorbent core 16 or any other layer of the absorbent article 10. The surge layer 17 can be located between the bodyside liner 14 and the absorbent core 16. Generally, the surge layer 17 can be constructed of any woven or nonwoven material that is easily penetrated by bodily exudates. For example, the surge layer 17 can include a nonwoven fabric layer composed of a meltblown or spunbond web of polyolefin or polyester filaments. Such a nonwoven fabric layer can include conjugate, biconstituent, and homopolymer fibers of staple or other lengths and mixtures of such fibers with other types of fibers. The surge layer 17 can also be a bonded carded web or an airlaid web composed of natural and/or synthetic fibers. The bonded carded web can, for example, be a powder bonded carded web, an infrared bonded carded web, or a through-air bonded carded web. A bonded carded web can optionally include a mixture or blend of different fibers. The surge layer 17 typically has a basis weight of less than about 150 gsm, and in various aspects, from about 10 gsm to about 150 gsm or about 30 gsm to about 150 gsm.

The surge layer 17 can be attached to one or more of various components in the absorbent article 10 such as the absorbent core 16, the bodyside liner 14, or the core wrap 20 by methods known in the art, such as by using an adhesive. Examples of suitable surge layers 17 are described in U.S. Pat. Nos. 5,486,166 and 5,490,846. Other suitable surge management materials are described in U.S. Pat. No. 5,820,973. The entire disclosures of these patents are hereby incorporated by reference herein to the extent they are not in conflict herewith.

A panty liner, not shown, is a relatively thin absorbent pad having a thickness of about 1 cm or less. Desirably, the thickness of a panty liner is less than about 0.5 cm. A panty liner can have a length of from between about 15 cm to about 50 cm and a width of from between about 2 cm to about 15 cm. The panty liner can have a rectangular, hourglass, or asymmetrical configuration and can contain the same components as the pad 10 shown in FIGS. 1 and 2, or at least the bodyside liner 14, the surge layer 17, an absorbent core 16, and an outer cover 15.

Disposable absorbent articles generally include an absorbent core or structure 16 as described herein. The absorbent core 16 of the present disclosure includes a series of alternating ridges and grooves extending in the longitudinal direction of the absorbent core 16. The absorbent core 16 can generally be produced in a number of ways. First, multiple layers of UCTAD material are stacked, and then the stack is embossed to produce the ridges and grooves (described below in association with FIG. 4). In another way, each layer of UCTAD material can be embossed to produce the ridges and grooves. The each embossed layer is stacked to form the absorbent core 16 (described below in association with FIG. 5). In such a stacking, the layers can be stacked such that the ridges of one layer directly abut the ridges on an adjacent layer, or the layers can be stacked such that the ridges of one layer nest in the grooves of an adjacent layer. Any other suitable arrangement can also be used.

In one aspect, multiple layers or plies of UCTAD tissue made with Northern Softwood Kraft (NSWK) and hardwood/eucalyptus cellulosic fibers that have longitudinal lines embossed into them can be used as an absorbent core, replacing prior art fluff pulp/superabsorbent material (SAM) mixtures. The embossed plies of UCTAD provide superior distribution along the length of the pad as well as equivalent liquid absorption/retention capacity without the use of SAM or synthetic fibers. For this aspect, the number of plies found to be optimal is 3 to 4 plies, but any suitable number of plies can be used.

Figure 3:
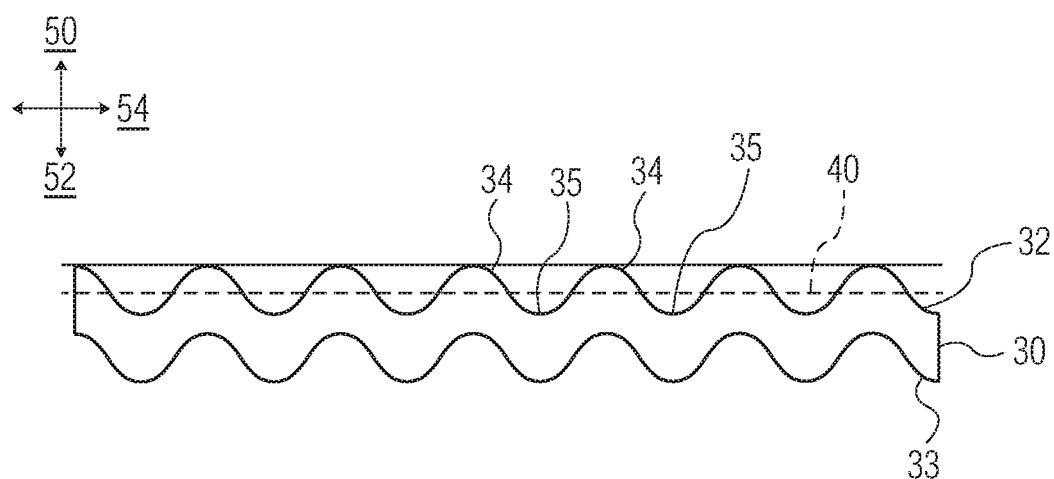
FIG. 3 is an elevation view of a cross-section of a sheet of UCTAD material, exaggerated to show detail.

It has also been observed that creating multilayered structures with UCTAD material and then mechanically embossing a pattern of longitudinal lines on the multilayered structure to create a channel-like pattern on the UCTAD material helps to further improve the liquid transport properties of the UCTAD-tissue-based absorbent structure. FIG. 3 illustrates a cross-section of a portion of a sheet 30 of UCTAD material, exaggerated to show detail and therefore not to scale. In a particular aspect, the sheet 30 includes fibers that are entirely natural fibers and preferably entirely cellulose fibers. The sheet 30 preferably has a basis weight range from about 10 gsm to about 120 gsm, and a rush transfer value from about 5% to about 70%. The sheet 30 includes opposing sheet surfaces 32, 33, each having a textured surface. Each surface 32, 33 includes an average material plane 40, a plurality of ridges 34 extending in a z-direction 50 from the average material plane 40, and a plurality of grooves 35 alternating with the plurality of ridges 34, wherein the grooves 35 have a depth extending in the opposite z-direction 52 from the average material plane 40. The grooves 35 have an average depth of about 0.5 mm to about 1 mm and an average frequency in the x-direction 54 of about 0.2 grooves/mm to about 0.5 grooves/mm. The sheet 30 has a longitudinal y-direction (not shown, into the page), where the grooves 35 extend the full length of the sheet 30 in the longitudinal direction.

Figure 4:
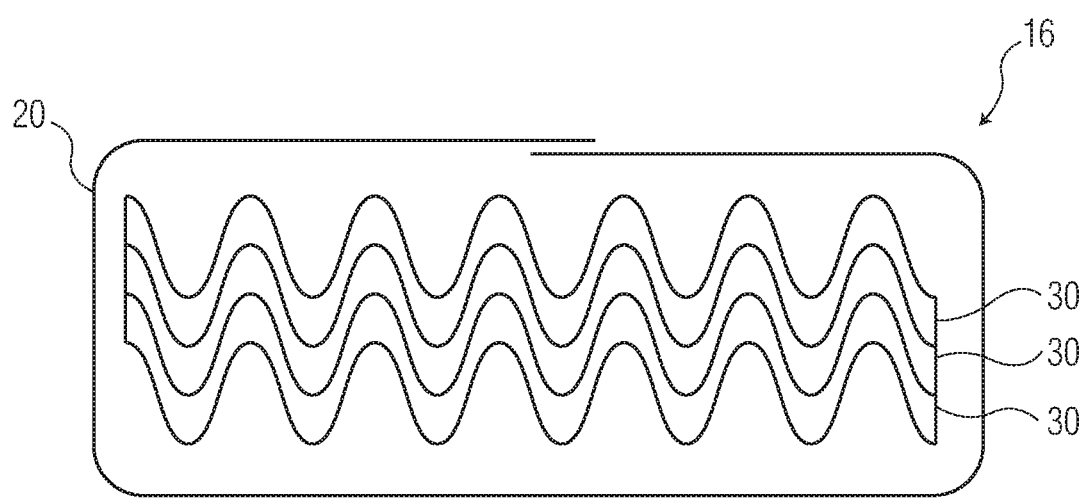
FIG. 4 is a cutaway elevation view of an absorbent core with UCTAD material and an optional core wrap where layers are stacked prior to embossing, and where portions are exaggerated to show detail.

Referring to FIG. 4, the present disclosure is directed to an absorbent core 16 that can be made from one or more sheets 30 of UCTAD material folded or layered and aligned to form the absorbent core 16. The sheets 30 of UCTAD material can be folded over on itself or multiple layers can be aligned and then bonded using, for example, adhesives, heat, and/or pressure. If folded, the folding of a sheet 30 of UCTAD material over onto itself can be accomplished through the use of conventional sheet folding means such as curved plates that work the UCTAD material over onto itself. Alternatively, separate sheets 30 of UCTAD material can be provided and stacked or aligned to provide an absorbent core 16 with multiple layers.

Figure 5:
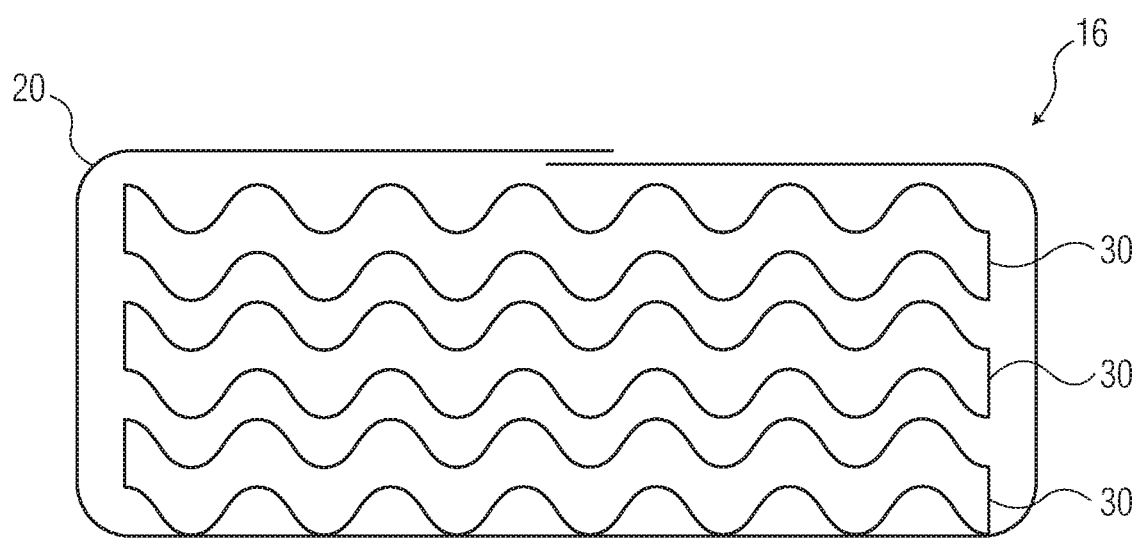
FIG. 5 is a cutaway elevation view of an absorbent core with UCTAD material and an optional core wrap where layers are embossed and then stacked, and where portions are exaggerated to show detail.

Referring to FIG. 5, the present disclosure is directed to an absorbent core 16 that can be made from one or more sheets 30 of UCTAD material folded or layered and aligned to form the absorbent core 16. Prior to stacking, each sheet 30 is embossed to produce ridges and grooves. A sheet 30 of UCTAD material can be folded over on itself or multiple layers can be aligned and then bonded using, for example, adhesives, heat, and/or pressure. If folded, the folding of a sheet 30 of UCTAD material over onto itself can be accomplished through the use of conventional sheet folding means such as curved plates that work the UCTAD material over onto itself. Alternatively, separate sheets 30 of UCTAD material can be provided and stacked or aligned to provide an absorbent core 16 with multiple layers.

An example of a suitable cellulosic material that can be used as an UCTAD material is an uncreped through-air dried (UCTAD) sheet having a basis weight of about 30 gsm to about 120 gsm. The UCTAD sheet can be prepared by the process disclosed in U.S. Pat. No. 5,048,589 issued to Crook et al. on Sep. 17, 1991 and U.S. Pat. No. 5,399,412 issued to Sudall et al. on Mar. 21, 1995, which are incorporated herein in their entireties to the extent they do not conflict herewith. Broadly, the process includes the steps of forming a furnish of cellulosic fibers, water, and a chemical wet strength resin; depositing the furnish on a traveling foraminous belt thereby forming a fibrous web on top of the traveling belt; subjecting the fibrous web to non-compressive drying to remove water from the fibrous web, and removing the dried fibrous web from the traveling foraminous belt.

In another aspect, a fluff pulp (typical softwood kraft/hardwood kraft blend) center with a top layer and a bottom layer of UCTAD tissue that have longitudinal lines embossed into them can also be used as the absorbent core in a menses-absorbing feminine care pad. The fluff pulp can be from an airlaid process, a typical hammermill fluff process, or any other suitable process. The UCTAD tissue can be separate plies or one ply folded around the fluff pulp. In these aspects, commercially-available UCTAD tissue does not provide comparable results versus the UCTAD tissue of the present disclosure.

The UCTAD tissue of the present disclosure is optimized for this product application through process settings, such as a rush transfer of 30% to 50% and a high MD/CD ratio, such as between 1.5 and 3. Optionally, the inclusion of bleached chemi-thermomechanical pulp (BCTMP) improves liquid absorption. Basis weights are in the range of 30 to 40 gsm per ply.

Stabilized cellulosic structures in which the capillary structure is stabilized and will not collapse during wetting will be advantageous for absorbing menses. One approach to make stabilized structures is using synthetic binder fibers combined with cellulosic pulp fibers and bonding the synthetic fibers using a thermal process. Another approach uses latex binders or a spray of hot melt adhesives to stabilize the structure. Meltblown polymer used in a coform process also creates a degree of stabilization.

All of these and other similar methods do not achieve complete bonding of the cellulosic fibers. As a result, all of the capillaries in the structure are not fully stabilized and capillary collapse of the unbonded cellulosic structure can occur while the structure is insulted with menses. This results in reduced absorbent utilization with large sections of the absorbent remaining free from menses while other sections of the absorbent are over-saturated and cause leakage.

To overcome the limitation of partially-stabilized cellulosic pulp based structures, the present disclosure uses wet-laid cellulosic material formed using the UCTAD process. This ensures complete bonding of all cellulosic fibers. The use of suitable additives such as kymene during the wet-laying process ensures a completely-stabilized absorbent that does not collapse on wetting with menses. The use of suitable cellulosic pulp fibers to form the UCTAD material further enhances the void volume and contributes to enhanced absorption and liquid distribution of menses. It has been observed that the superior properties of the UCTAD material enables the creation of absorbent structures for menses that do not require the use of superabsorbent particles.

Using suitable blends of pulp fibers consisting of northern softwood kraft pulp and bleached chemi-thermomechanical pulp to make the UCTAD material helps to provide a good balance of liquid retention and distribution properties for menses. The use of suitable process conditions for making the UCTAD, such as rush transfer, helps to create increased bulk and void volume for menses absorption and retention. The use of process conditions in the UCTAD process to orient cellulosic fibers in the machine direction enables enhanced liquid transport in the UCTAD material, thereby enhancing absorbent utilization.

Having multiple layers also provides for liquid transport between the layers. The contribution of interfacial liquid transport between the layers of UCTAD material helps to further enhance the flux of menses liquid that is transported. The channel-embossed pattern creates a higher density at the bottom of the channel (groove 35 in FIG. 3). The sides of the embossed channel have a lower density than the bottom. The menses liquid runs along the bottom of the channel and gets absorbed along the walls of the channel.

In some instances, the embossing of the multilayered UCTAD material can cause increased stiffness of the absorbent core. It is possible to avoid making the embossed structure stiff by mechanically softening the individual layers of UCTAD using a process such as ring-rolling. The stiffness of the embossed structure can also be reduced by using a small quantity of southern softwood kraft pulp and also adjusting the additive level of kymene.

It has been observed that this UCTAD-based absorbent structure provides improved absorbent utilization compared to structures stabilized by other means. The lack of superabsorbents and synthetic fiber and the use of higher speeds in the wet-laying process enables the creation of an absorbent material that provides better absorbent utilization at a reduced cost.

In an aspect, the UCTAD material is used as a carrier sheet for airform fiberized pulp. The UCTAD material is layered or folded to form a laminate with fiberized pulp between the UCTAD layers. The resulting structure is then embossed. The embossed laminate is soft and flexible, exhibited absorbent properties and liquid distribution that are comparable to the embossed multilayer UCTAD structure. This aspect demonstrates the benefit in using UCTAD as a carrier sheet to create thermally-bonded or hydrogen-bonded airlaid materials.

UCTAD material made with a high degree of machine-direction fiber orientation enhances liquid transport. The high degree of machine-direction fiber orientation results in high MD tensile strength but low CD tensile strength. The unconventional sheet structure of the present disclosure departs from conventional balanced UCTAD sheets with equal MD/CD strength. The resulting asymmetric sheet structure enhances liquid transport.

In addition, with respect to further enhancements, the use of specific blends of NSWK and BCTMP fibers has been shown to enhance absorption of menses. An optimal level of rush transfer around 40% has been shown to provide the best balance between absorbent capacity and liquid distribution property.

As a result, superior menses liquid absorption and distribution have been demonstrated without using superabsorbents or synthetic fibers. Using UCTAD as a carrier layer in an embossed hydrogen bonded or thermally bonded airlaid provides superior absorbent capacity and liquid distribution.

Figure 6:
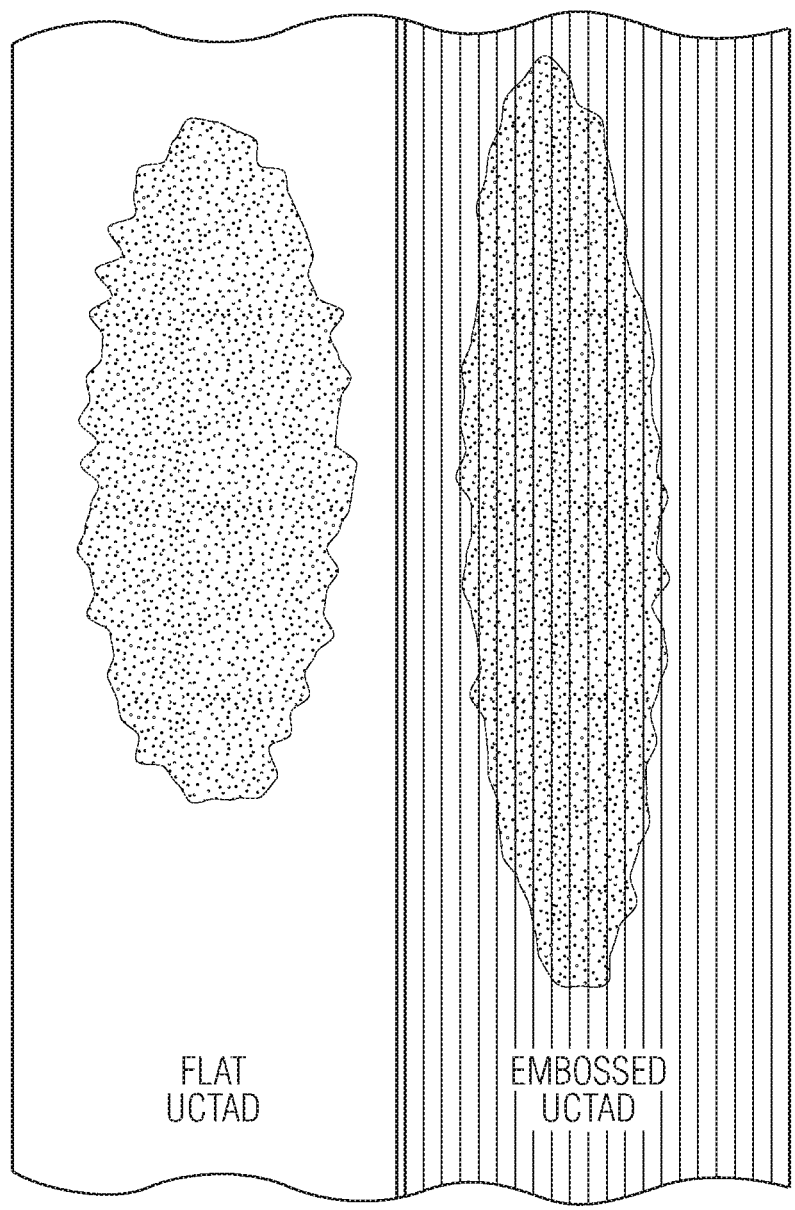
FIG. 6 is a schematic illustration of the distribution of menses simulant on standard flat UCTAD material and on the embossed UCTAD material of the present disclosure.
Figure 7:
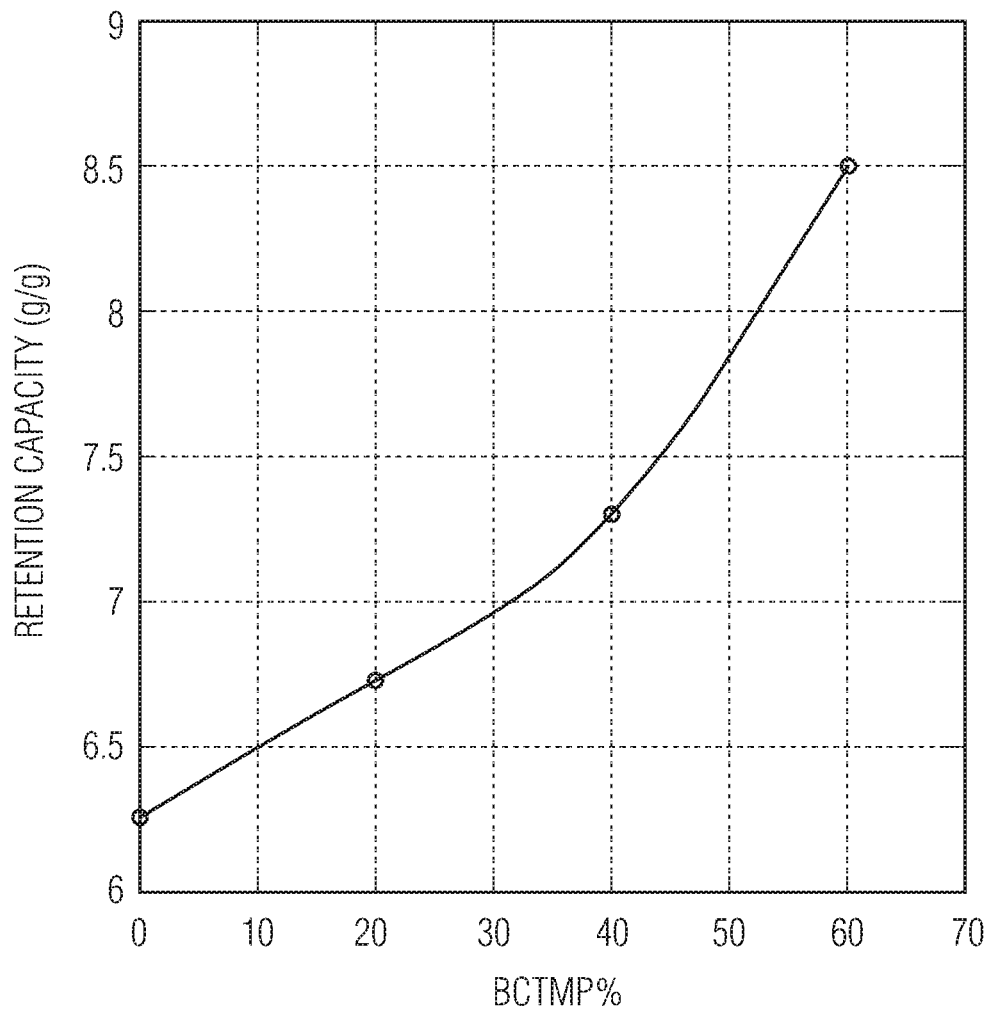
FIG. 7 is a graphical illustration of the relationship between BCTMP content and retention capacity.
Figure 8:
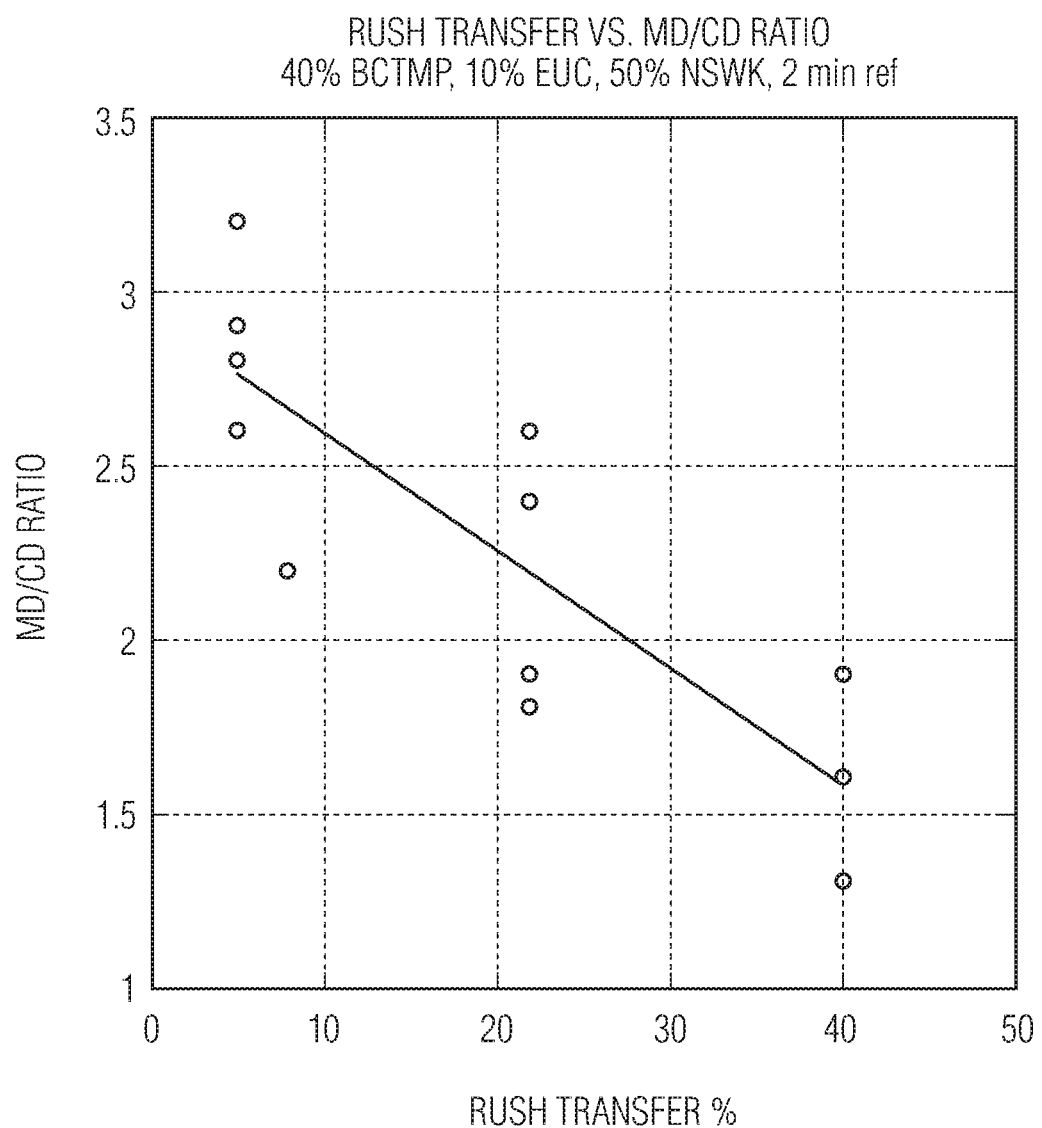
FIG. 8 is a graphical illustration of the relationship between rush transfer percentage and MD/CD ratio.
Figure 9:
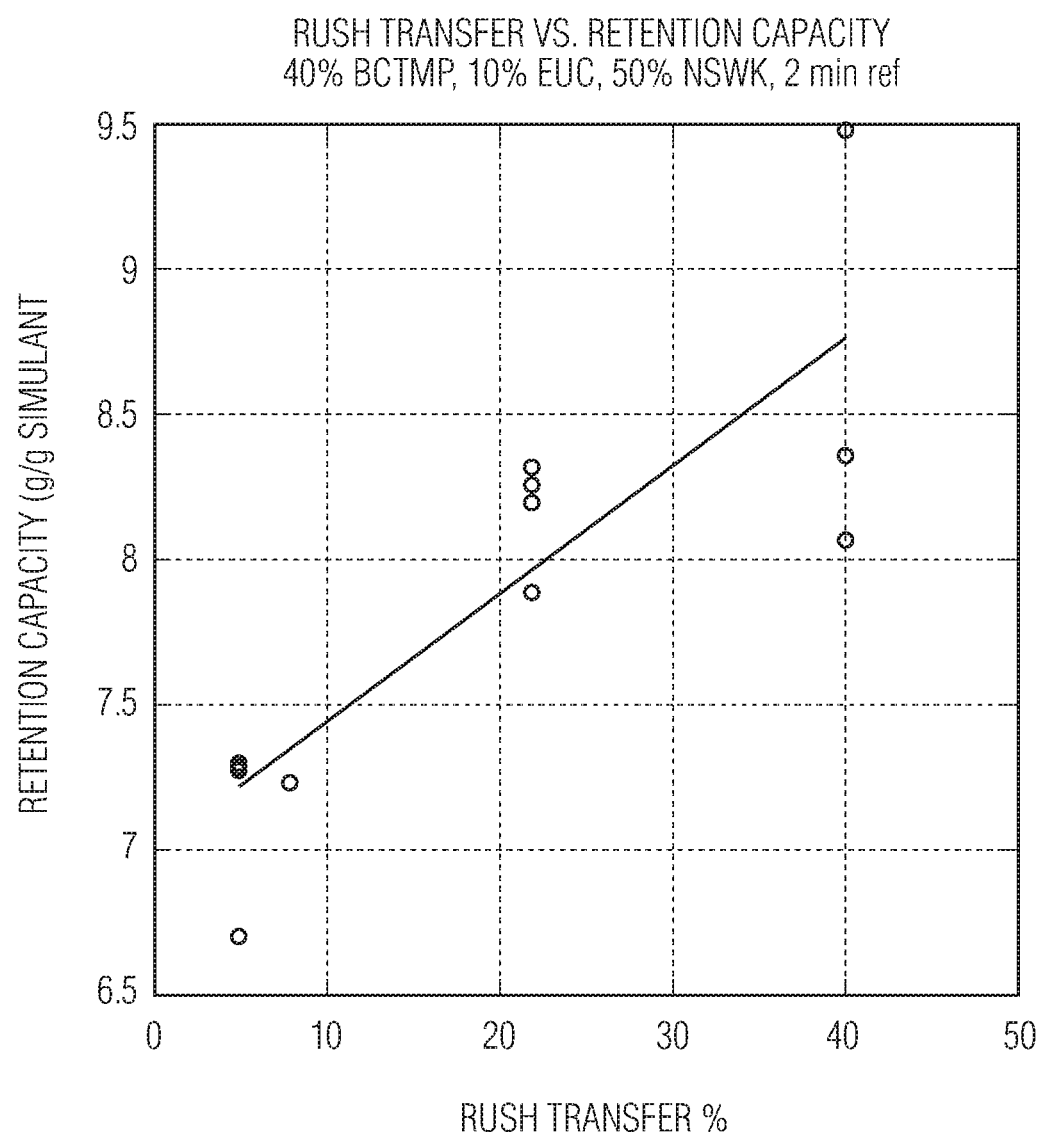
FIG. 9 is a graphical illustration of the relationship between rush transfer and retention capacity.
Figure 10:
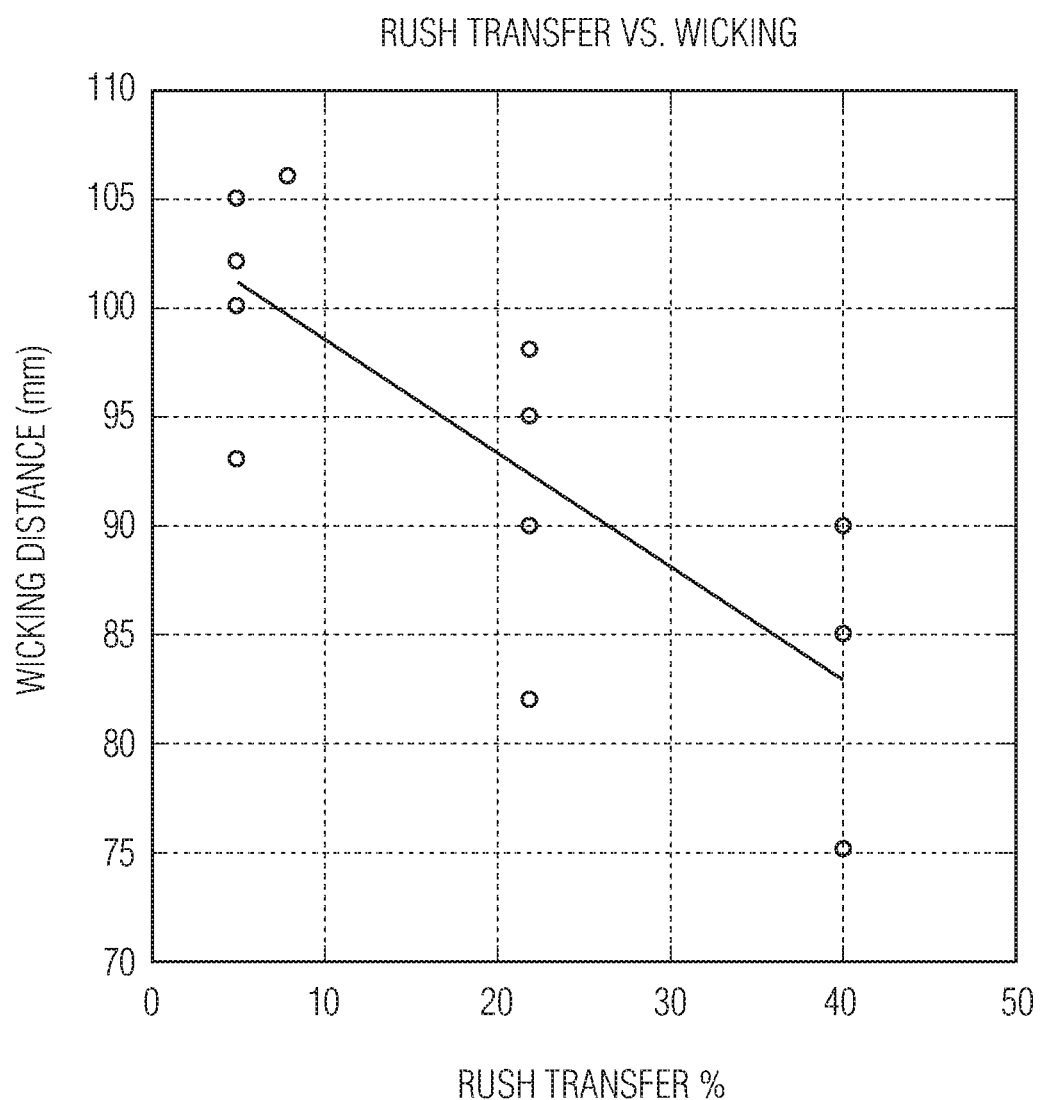
FIG. 10 is a graphical illustration of the relationship between rush transfer and wicking.

In testing the materials described herein, all tests were performed using menses simulant. It was found that the UCTAD material of the present disclosure demonstrated greater liquid distribution than that of standard UCTAD material (see FIG. 6). Increasing BCTMP content increased retention capacity but reduced liquid distribution (see FIG. 7). Increasing rush transfer decreased MD/CD ratio (see FIG. 8). Increasing rush transfer increased retention capacity but reduced liquid distribution (see FIGS. 9 and 10). Increasing NSWK content and the level of MD/CD fiber orientation increased liquid distribution. Decreasing through-air dried vacuum and using a more flat through-air dried fabric is beneficial for liquid handling, both capacity and distribution. Increasing basis weight also has a positive effect on capacity and distribution.

It was demonstrated that wicking and retention capacity are generally opposing properties in a base sheet, and that UCTAD materials with a balance of retention and distribution can be achieved. Further, the best of retention and the best of distribution can be combined through lamination. Also, it is possible to emboss a high retention structure with a suitable bond pattern to enhance liquid distribution.

In a first particular aspect, an absorbent article having a liquid-handling system includes a liquid permeable body-side liner; a liquid impermeable outer cover; and an absorbent core disposed between the liner and the outer cover, wherein the absorbent core has a longitudinal direction, wherein the absorbent core includes a layer of a three-dimensionally patterned, wetlaid, cellulosic tissue nonwoven material, and wherein the layer includes longitudinal ridges and grooves.

A second particular aspect includes the first particular aspect, wherein the absorbent core includes multiple layers of the three-dimensionally patterned, wetlaid, cellulosic tissue nonwoven material, and wherein each layer includes longitudinal ridges and grooves.

A third particular aspect includes the first and/or second aspect, wherein the multiple layers are at least three layers.

A fourth particular aspect includes one or more of aspects 1-3, wherein the absorbent core includes fluff pulp disposed between layers of the three-dimensionally patterned, wetlaid, cellulosic tissue nonwoven material.

A fifth particular aspect includes one or more of aspects 1-4, wherein two of the multiple layers are two portions of a sheet folded over against itself.

A sixth particular aspect includes one or more of aspects 1-5, wherein the multiple layers are joined by lines of embossing, such lines of embossing extending in the longitudinal direction.

A seventh particular aspect includes one or more of aspects 1-6, wherein the ridges and grooves of one layer are nested in the grooves and ridges of an adjacent layer.

An eighth particular aspect includes one or more of aspects 1-7, wherein each layer has opposing layer surfaces each having a textured surface, wherein each layer surface includes an average material plane, a plurality of ridges extending in a z-direction from the average material plane, and a plurality of grooves alternating with the plurality of ridges, the grooves having a depth, wherein the depth extends in the opposite z-direction from the average material plane.

A ninth particular aspect includes one or more of aspects 1-8, wherein the layer has a basis weight between 30 gsm and 40 gsm.

A tenth particular aspect includes one or more of aspects 1-9, wherein the absorbent core has an MD/CD ratio between 1.5 and 3.

An eleventh particular aspect includes one or more of aspects 1-10, wherein the absorbent core has a rush transfer between 30 percent and 50 percent.

A twelfth particular aspect includes one or more of aspects 1-11, wherein the layer includes bleached chemi-thermomechanical pulp (BCTMP).

A thirteenth particular aspect includes one or more of aspects 1-12, wherein the absorbent article is a feminine pad or panty liner.

In a fourteenth particular aspect, an absorbent article having a liquid-handling system includes a liquid permeable bodyside liner; a liquid impermeable outer cover; and an absorbent core disposed between the liner and the outer cover, wherein the absorbent core has a longitudinal direction, wherein the absorbent core includes multiple layers of a three-dimensionally patterned, wetlaid, cellulosic tissue nonwoven material, wherein each layer of the multiple layers includes longitudinal ridges and grooves, and wherein the multiple layers are joined by lines of embossing, such lines of embossing extending in the longitudinal direction.

A fifteenth particular aspect includes the fourteenth particular aspect, wherein the absorbent core includes fluff pulp disposed between layers of the three-dimensionally patterned, wetlaid, cellulosic tissue nonwoven material.

A sixteenth particular aspect includes the fourteenth and/or fifteenth aspect, wherein two of the multiple layers are two portions of a sheet folded over against itself.

A seventeenth particular aspect includes one or more of aspects 14-16, wherein the multiple layers are at least three layers.

In an eighteenth particular aspect, an absorbent article having a liquid-handling system includes a liquid permeable bodyside liner; a liquid impermeable outer cover; and an absorbent core disposed between the liner and the outer cover, wherein the absorbent core has a longitudinal direction, wherein the absorbent core includes multiple layers of a three-dimensionally patterned, wetlaid, cellulosic tissue nonwoven material, and wherein each layer of the multiple layers includes embossed longitudinal ridges and grooves.

A nineteenth particular aspect includes the eighteenth particular aspect, wherein the absorbent core includes fluff pulp disposed between layers of the three-dimensionally patterned, wetlaid, cellulosic tissue nonwoven material.

A twentieth particular aspect includes the eighteenth and/or nineteenth aspects, wherein two of the multiple layers are two portions of a sheet folded over against itself.

While the disclosure has been described in detail with respect to the specific aspects thereof, it will be appreciated that those skilled in the art, upon attaining an understanding of the foregoing, can readily conceive of alterations to, variations of, and equivalents to these aspects. Accordingly, the scope of the present disclosure should be assessed as that of the appended claims and any equivalents thereto.

What is claimed is:

1. An absorbent article having a liquid-handling system, the article comprising:
    a liquid permeable bodyside liner;
    a liquid impermeable outer cover;
    an absorbent core free of superabsorbent material disposed between the liner and the outer cover, wherein the absorbent core has a longitudinal direction, wherein the absorbent core includes multiple layers of a three-dimensionally patterned, wetlaid, cellulosic tissue nonwoven material, and wherein each of the layers includes embossed grooves forming longitudinally extending ridges and grooves, the longitudinally extending ridges and grooves of adjacent layers being nested together, wherein the embossed grooves having a greater density than the ridges; and
    a transfer layer disposed between the absorbent core and the liquid permeable bodyside liner, the transfer layer formed of a nonwoven web of synthetic fibers.

2. The absorbent article of claim 1, wherein the multiple layers are at least three layers.

3. The absorbent article of claim 1, wherein the absorbent core includes fluff pulp disposed between layers of the three-dimensionally patterned, wetlaid, cellulosic tissue nonwoven material.

4. The absorbent article of claim 1, wherein two of the multiple layers are two portions of a sheet folded over against itself.

5. The absorbent article of claim 1, wherein each layer has opposing layer surfaces each having a textured surface, wherein each layer surface includes an average material plane, a plurality of ridges extending in a z-direction from the average material plane, and a plurality of grooves alternating with the plurality of ridges, the grooves having a depth, wherein the depth extends in the opposite z-direction from the average material plane.

6. The absorbent article of claim 1, wherein the layer has a basis weight between 30 gsm and 40 gsm.

7. The absorbent article of claim 1, wherein the absorbent core has an MD/CD ratio between 1.5 and 3.

8. The absorbent article of claim 1, wherein the absorbent core has a rush transfer between 30 percent and 50 percent.

9. The absorbent article of claim 1, wherein the layer includes bleached chemi-thermomechanical pulp (BCTMP).

10. The absorbent article of claim 1, wherein the absorbent article is a feminine pad or panty liner.

11. The absorbent article of claim 1, further comprising a corewrap surrounding the three-dimensionally patterned, wetlaid, cellulosic tissue nonwoven material.

12. The absorbent article of claim 1, wherein the three-dimensionally patterned, wetlaid, cellulosic tissue nonwoven material is un-apertured.

13. An absorbent article having a liquid-handling system, the article comprising:
   a liquid permeable bodyside liner;
   a liquid impermeable outer cover; and
   an absorbent core free of superabsorbent material disposed between the liner and the outer cover, wherein the absorbent core has a longitudinal direction, wherein the absorbent core comprises a corewrap surrounding the absorbent core, wherein the absorbent core comprises multiple layers of a three-dimensionally patterned, wetlaid, cellulosic tissue nonwoven material, wherein each layer of the multiple layers includes longitudinally extending ridges and grooves with the longitudinally extending ridges and grooves of adjacent layers being nested together, and wherein the multiple layers are joined by lines of embossing extending in the longitudinal direction and forming the ridges and grooves.

14. The absorbent article of claim 13, wherein the absorbent core includes fluff pulp disposed between layers of the three-dimensionally patterned, wetlaid, cellulosic tissue nonwoven material.

15. The absorbent article of claim 13, wherein two of the multiple layers are two portions of a sheet folded over against itself.

16. The absorbent article of claim 13, wherein the multiple layers are at least three layers.

17. An absorbent article having a liquid-handling system, the article comprising:
   a liquid permeable bodyside liner;
   a liquid impermeable outer cover; and
   an absorbent core free of superabsorbent material disposed between the liner and the outer cover, wherein the absorbent core has a longitudinal direction, wherein the absorbent core comprises a corewrap surrounding multiple layers of a three-dimensionally patterned, wetlaid, cellulosic tissue nonwoven material, and wherein each layer of the multiple layers is unapertured and includes embossed grooves forming longitudinally extending ridges and grooves with the longitudinally extending ridges and grooves of adjacent layers being nested together
   wherein the absorbent core includes fluff pulp disposed between layers of the three-dimensionally patterned, wetlaid, cellulosic tissue nonwoven material.

18. The absorbent article of claim 17, wherein two of the multiple layers are two portions of a sheet folded over against itself.

* * * * *